United States Patent
Bajaj et al.

(10) Patent No.: US 10,107,730 B2
(45) Date of Patent: Oct. 23, 2018

(54) DROP WEIGHT TOWER FOR CRACK INITIATION IN FRACTURE MECHANICS SAMPLES

(71) Applicant: SABIC Global Technologies, B.V., Bergen op Zoom (NL)

(72) Inventors: Devendra Bajaj, Evansville, IN (US); David Kay, Mount Vernon, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/545,082

(22) PCT Filed: Jul. 8, 2016

(86) PCT No.: PCT/US2016/041596
§ 371 (c)(1),
(2) Date: Jul. 20, 2017

(87) PCT Pub. No.: WO2017/011332
PCT Pub. Date: Jan. 19, 2017

(65) Prior Publication Data
US 2018/0010993 A1 Jan. 11, 2018

Related U.S. Application Data

(60) Provisional application No. 62/190,866, filed on Jul. 10, 2015.

(51) Int. Cl.
*G01N 3/00* (2006.01)
*G01N 3/303* (2006.01)

(52) U.S. Cl.
CPC ....... *G01N 3/303* (2013.01); *G01N 2203/006* (2013.01); *G01N 2203/0033* (2013.01); *G01N 2203/0064* (2013.01)

(58) Field of Classification Search
CPC ........... G01N 3/303; G01N 2203/0033; G01N 2203/0064
(Continued)

(56) References Cited

U.S. PATENT DOCUMENTS

| | | |
|---|---|---|
| 2,001,087 A | 5/1935 | Herbert Abramson |
| 2,475,614 A | 7/1949 | Hoppmann et al. |

(Continued)

OTHER PUBLICATIONS

International Search Report and Written Opinion from PCT/US2016/041596, dated Sep. 19, 2016.
(Continued)

*Primary Examiner* — Max Noori
(74) *Attorney, Agent, or Firm* — Cantor Colburn LLP

(57) ABSTRACT

Drop-weight tower (110) for reproducibly initiating a crack in a material sample for fracture mechanics testing comprising a base (120) with a top surface upon which a sample holder (124) is mounted to grip a material sample, an attachment column (140) having a linear rail (142), a carriage (162) attached to the linear rail (142) and a stage (164) is attached to the carriage. The stage (164) includes a vertical rod (184) and a razor-blade holder (178). A weight is slidably mounted to the vertical rod (184). The carriage is used to adjust the height of the stage (164) relative to the material sample. A hammer (180) slides up and down the vertical rod (184) to apply consistent and reproducible force on the razor (178) that then initiates the crack in the material sample.

21 Claims, 14 Drawing Sheets

(58) Field of Classification Search
USPC .................................................. 73/12.09
See application file for complete search history.

(56) References Cited

U.S. PATENT DOCUMENTS

| | | | | |
|---|---|---|---|---|
| 5,457,984 A * | 10/1995 | Ambur | ................... | G01N 3/303 |
| | | | | 73/12.09 |
| 5,739,411 A * | 4/1998 | Lee | .................... | G01N 3/48 |
| | | | | 73/12.09 |
| 6,523,391 B1 * | 2/2003 | Knox | ................ | G01M 7/08 |
| | | | | 73/12.01 |
| 2011/0146376 A1 * | 6/2011 | Subert | ................ | E02D 1/02 |
| | | | | 73/12.06 |
| 2013/0076902 A1 * | 3/2013 | Gao | .................... | B25J 9/042 |
| | | | | 348/148 |
| 2014/0026635 A1 * | 1/2014 | Zorn | .................... | G01N 3/24 |
| | | | | 73/12.06 |
| 2014/0305186 A1 * | 10/2014 | Touma | ................ | G01N 3/303 |
| | | | | 73/12.06 |
| 2015/0114084 A1 * | 4/2015 | He | .................... | G01M 7/08 |
| | | | | 73/12.13 |

OTHER PUBLICATIONS

Lee et al., "Assessment of Impact Characteristics for Incipient Crack Formation in Polymeric Materials," Instrumented Impact Testing ofPlastics and Composite Materials, ASTM STP936, pp. 324-334, 1987.

Manigrasso et al., "Characterization of a Closed Femur Fracture Model in Mice," J Orthop Trauma. Nov.-Dec. 2004, pp. 687-695, vol. 18 No. 10.

Marturano et al., "An Improved Murine Femur Fracture Device for Bone Healing Studies," Journal of Biomechanics, pp. 1222-1228. 2008, vol. 41 Issue (6).

* cited by examiner

Manual Method

FIG. 13 Manual Method

DROP WEIGHT TOWER FOR CRACK INITIATION IN FRACTURE MECHANICS SAMPLES

CROSS-REFERENCE TO RELATED APPLICATIONS

This application is a 371 of PCT patent application Ser. No. PCT/US2016/041596, filed Jul. 8, 2016, which claims priority to U.S. Provisional Patent Application Ser. No. 62/190,866, filed Jul. 10, 2015.

BACKGROUND

The present disclosure relates to methods and devices for fracture mechanics testing. In particular, a drop weight tower is described for initiating a sharp crack in a test material sample. The apparatus has design features intended to increase repeatability and reproducibility of testing conditions.

Fracture mechanics is used to study the initiation and propagation of cracks in materials. The presence of cracks, which may develop over time in a material, can modify the local stresses around cracks, due to stress concentration, such that previous stress analyses of the material are inadequate. Once a crack reaches a critical length, it can propagate through the structure and cause catastrophic material failure. This can occur for many reasons, such as uncertainties in loading or operating environments, material defects, design flaws, construction deficiencies, or failing to perform maintenance. By initiating a crack in a material sample, quantitative relations between the crack length, the material's inherent resistance to crack growth, and the stress at which the crack propagates to cause structural failure can be calculated. Thus, fracture mechanics testing requires initiation of a sharp crack (also sometimes referred as a pre-crack) in the test sample.

Crack initiation in brittle material samples is traditionally achieved by a razor tap method. In this method, a test sample is gripped by a bench vise and a razor blade is held in contact with the test sample. A hammer is then manually dropped on the razor blade to initiate a crack in the test sample. FIG. 1 is a picture showing the shape of the test sample. However, there is limited control over the energy of impact, and therefore the length of crack, which results in poor repeatability and reproducibility of the process. These issues with a conventional razor tap method were previously addressed by 1) minimizing operator error by practicing and improving the operator experience and 2) increasing the number of samples to account for process variability.

It would be desirable to provide a testing apparatus that can provide controlled initiation of a crack in a material sample in a consistent and reproducible manner.

BRIEF DESCRIPTION

The present disclosure relates to apparatuses and methods for controlled initiation of a crack in a material test sample. A drop weight tower includes a flat horizontal base with a sample holder. A vertical attachment column has a linear rail. Mounted on the linear rail is a carriage assembly having a stage extending therefrom. A razor blade holder is located on the bottom surface of the stage, and a hammer assembly is on the top surface of the stage, these parts are positioned over the sample holder. The hammer assembly includes a weight that slides down a vertical rod. In use, the carriage assembly is lowered, such that the razor blade rests upon the material test sample. The weight is then lifted to a marked location and released to slide down the rod. The carriage assembly can be locked in place with a safety lever, and the vertical travel can be controlled by a pneumatic cylinder. The speed of the vertical travel can be controlled by adjusting the air flow through the cylinder.

Disclosed in various embodiments are drop weight towers for initiating a crack in a material sample for fracture mechanics testing, comprising: (a) a base having a top surface, and a sample holder mounted on the top surface for gripping the sample; (b) an attachment column extending upward from the top surface of the base at a first vertical location, the attachment column including a linear rail; (c) a carriage assembly attached to the linear rail of the attachment column, the carriage assembly including: (i) a carriage capable of sliding up and down along the linear rail of the attachment column; and (ii) a stage extending perpendicular to the linear rail, the stage having a first end that is attached to the carriage, a second end distal from the carriage, a top surface, and a bottom surface; (d) a razor blade holder on the bottom surface at the second end of the stage, located over the sample holder; and (e) a hammer assembly on the top surface at the second end of the stage in-line with the razor blade holder, comprising: (i) a vertical rod; and (ii) an annular weight surrounding the vertical rod and operable to slide along the vertical rod.

The annular weight can be formed from a pipe concentrically surrounding the vertical rod and having a first threaded end and a second threaded end, to which a weighted cylinder can be attached. A ball bearing assembly is usually placed between the weight and the vertical rod to reduce friction.

The hammer assembly may further include an adjustable stopper attached to the vertical rod above the annular weight, the adjustable stopper acting as a starting drop point for the annular weight.

The razor blade holder of the hammer assembly may be a spring loaded clamp.

The drop weight tower may further comprise a safety lever extending from the attachment column, the safety lever having a locked position for holding the carriage assembly at a specified height and an unlocked position for allowing the carriage assembly to move up and down the linear rail. The safety lever can be spring loaded.

The drop weight tower can further comprise a pneumatic cylinder mounted on a pillar proximate to the attachment column, the pneumatic cylinder being connected to a handle on the carriage assembly. The pneumatic cylinder usually includes a valve for adjusting the air flow through the cylinder.

The sample holder may be in the form of a vise. The drop weight tower can further comprise a razor blade which is separable from the razor blade holder.

Also disclosed are methods for initiating a crack in a material sample for fracture mechanics testing, comprising: receiving a drop weight tower that comprises: (a) a base having a top surface, and a sample holder mounted on the top surface for gripping the sample; (b) an attachment column extending upward from the top surface of the base at a first vertical location, the attachment column including a linear rail; (c) a carriage assembly attached to the linear rail of the attachment column, the carriage assembly including: (i) a carriage capable of sliding up and down along the linear rail of the attachment column; and (ii) a stage extending perpendicular to the linear rail, the stage having a first end that is attached to the carriage, a second end distal from the carriage, a top surface, and a bottom surface; (d) a razor blade holder on the bottom surface at the second end of the stage, located over the sample holder; and (e) a hammer assembly on the top surface at the second end of the stage in-line with the razor blade holder, comprising: (i) a vertical rod; and (ii) an annular weight surrounding the vertical rod and operable to slide along the vertical rod; mounting the material sample in the sample holder; mounting a razor blade in the razor blade holder; lowering the carriage along the linear rail until the razor blade rests on the material sample; raising the annular weight to a desired height along the vertical rod; initiating a crack in the material sample by releasing the annular weight to travel down the vertical rod to create an impact force that causes the razor blade to initiate the crack in the material sample.

Sometimes, the method can further comprise using an adjustable stopper to mark the height from which the annular weight can be released. Other times, the method can further comprise raising the carriage assembly along the linear rail until a safety lever locks the carriage in place at a specified height.

The method can further comprise providing a pneumatic cylinder attached to the carriage assembly and having a valve. The valve can be adjusted to increase or decrease the speed which the carriage assembly can vertically travel along the linear rail.

These and other non-limiting aspects and/or objects of the disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
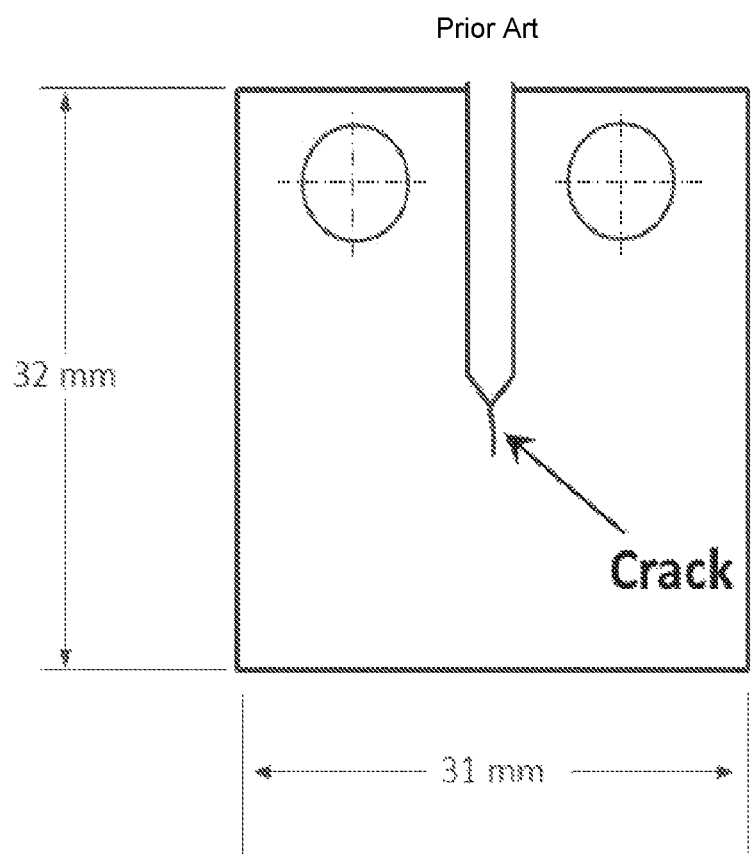
FIG. 1 is a schematic showing the typical shape of a CT material sample used in fracture mechanics testing.

A more complete understanding of the devices and methods disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. In the specification and the claims which follow, reference will be made to a number of terms, which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing devices or methods as "consisting of" and "consisting essentially of" the enumerated components/steps, which allows the presence of only the named components/steps, and excludes other components/steps.

Numerical values in the specification and claims of this application should be understood to include (i) numerical values which are the same when reduced to the same number of significant figures and (ii) numerical values which differ from the stated value by less than the experimental error of conventional measurement technique of the type described in the present application to determine the value.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

In describing the device, the terms "upper" and "lower" are used to describe the orientation of different components relative to an axis of the device.

Some terms used herein are relative terms. For example, the terms "upper" and "lower" are relative to each other in location, i.e. an upper component is located at a higher elevation than a lower component along a vertical axis. The upper end of a first component and the upper end of a second component are both oriented in the same direction on the axis, as are their lower ends.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "upwards" and "downwards" are also relative to an absolute reference; an upwards flow is always against the gravity of the earth.

The term "thermoset" refers to a polymer that irreversibly cross-links upon curing, so that the thermoset polymer cannot be melted and re-shaped after curing. Examples of thermoset polymers include epoxies.

The term "thermoplastic" refers to a polymer whose chains associate through intermolecular forces. Thus, a thermoplastic polymer can be reshaped by heating. Examples of thermoplastic polymers include polyetherimides, polycarbonates, polyethylene, polypropylene, and polystyrene.

The term "razor blade" is used herein to refer to any object having a cutting edge. This term should not be construed as setting any limit on the size of the razor blade or the shape of the cutting edge.

The present disclosure relates to sample material testing devices, in particular, to a drop weight tower for initiating a crack in a fracture mechanics test sample material. The drop weight tower has a base for supporting various assemblies, such as an attachment column for supporting a linear rail, a carriage assembly capable of sliding up and down the linear rail, a hammer assembly for supporting a weight, and a razor blade holder. The drop weight tower is operated by raising the weight to a specified height and releasing the weight to cause a razor blade to initiate a crack in a material sample.

FIG. 1 is a schematic (front view) of a typical compact tension (CT) specimen used in fracture mechanics testing. As will be appreciated by those skilled in the art, the test specimen can be made of any suitable material where it is desired to measure the inherent resistance to crack growth. As will also be appreciated, the test specimen can be made in any desired dimension from any suitable method. For example, the test sample can be an epoxy material, cast in a negative silicone mold having compact tension geometry or machined from an injection or compression molded piece of thermoplastic. The geometry of the test sample should permit the gripping of the sample by a suitable sample holder. In particular embodiments, the test sample can have a width of about 31 millimeters (mm) and a height of about 32 mm with a thickness of about 8 mm. FIG. 1 also shows the location at which the crack is initiated.

Figure 2:
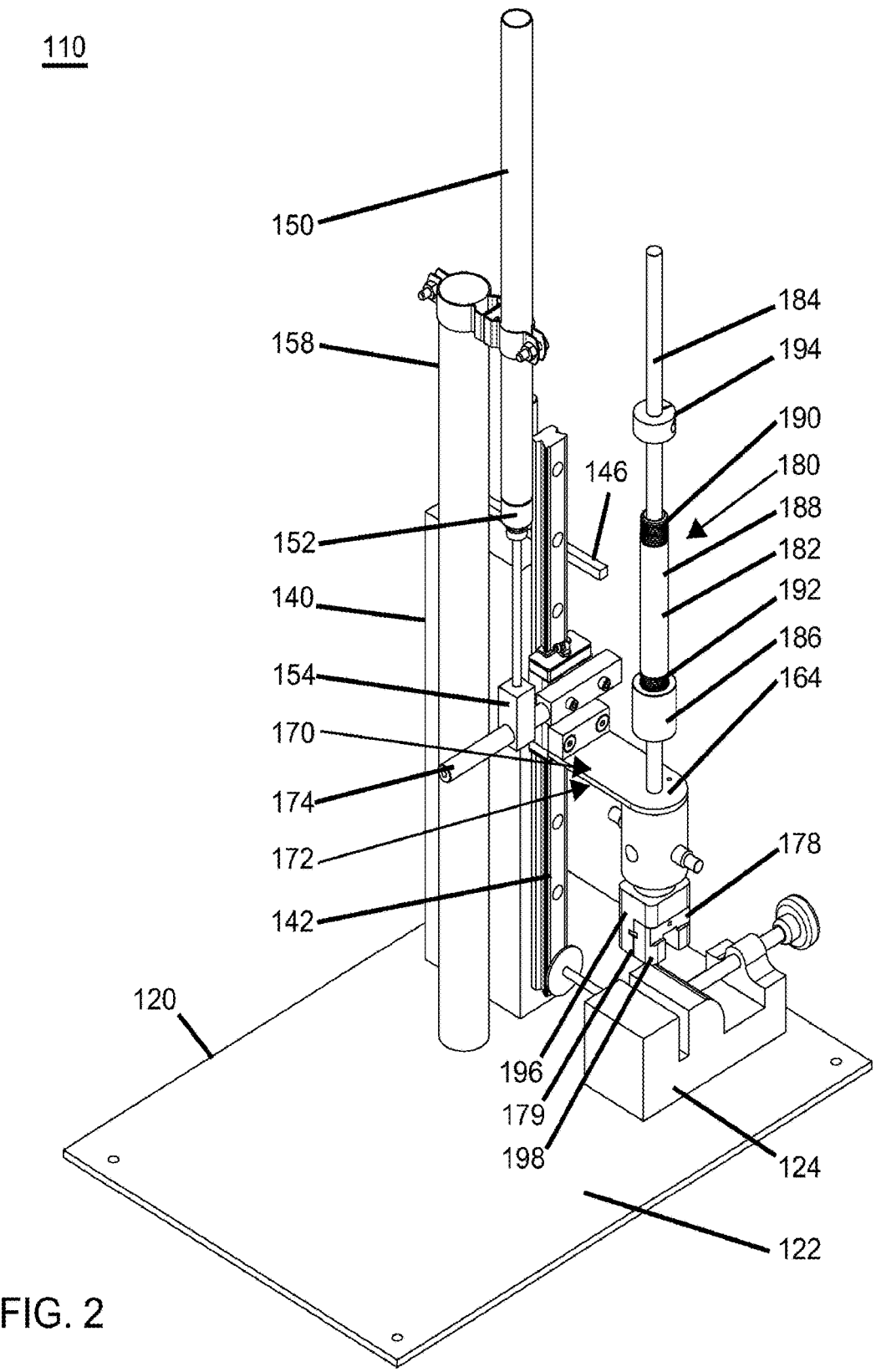
FIG. 2 is a first perspective picture of a drop weight tower for crack initiation according to a first exemplary embodiment of the present disclosure.
Figure 3:
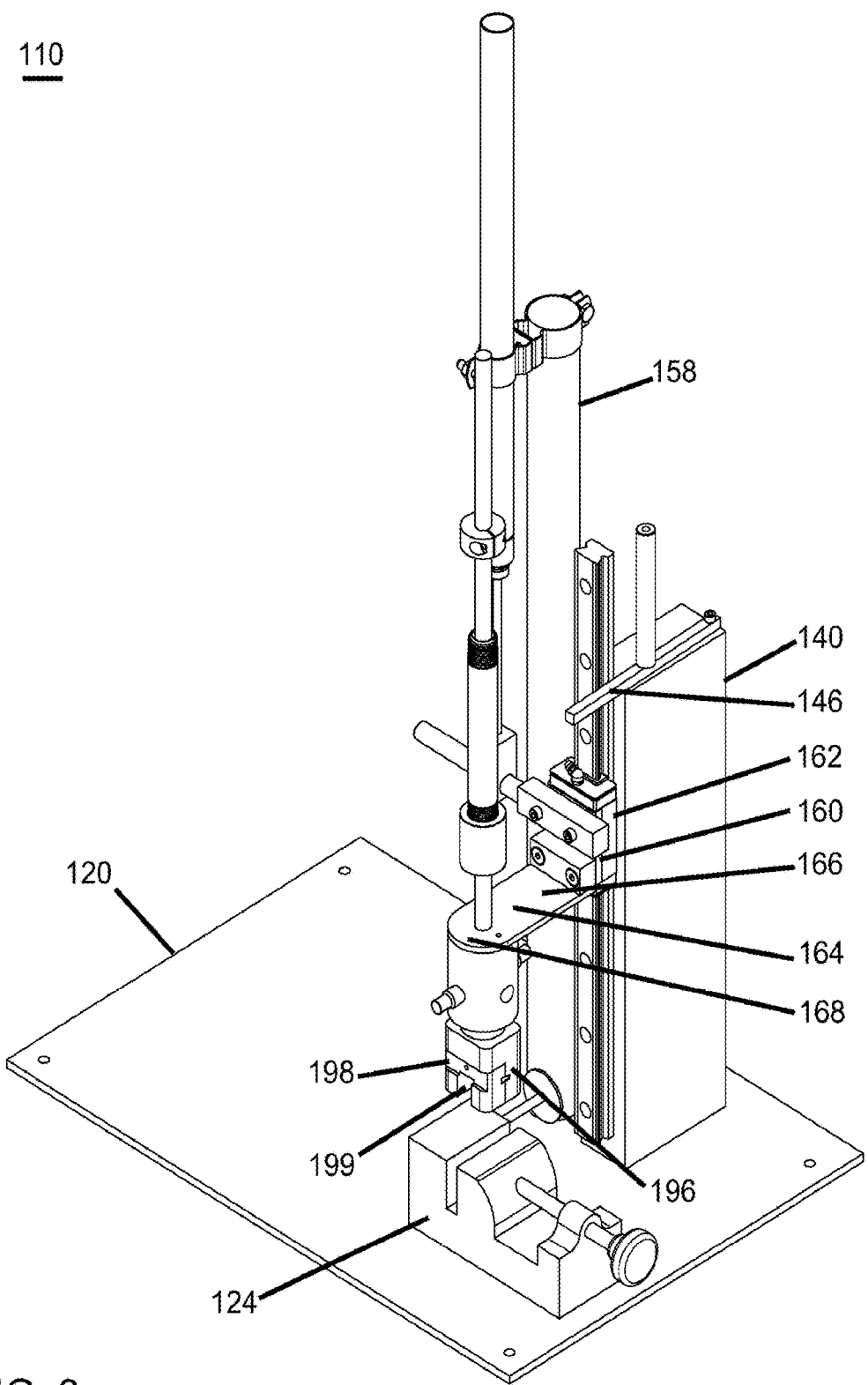
FIG. 3 is a second perspective picture of the drop weight tower from a perspective approximately 90 degrees different from that of FIG. 2.

FIG. 2 and FIG. 3 are different views of an exemplary drop weight tower of the present disclosure. FIG. 2 is a first perspective view of the drop weight tower. FIG. 3 is a second perspective view, taken at approximately 90 degrees from that of FIG. 2.

The drop weight tower 110 is used to initiate a crack in a material sample (not illustrated here). The tower includes a base 120, which has a top surface 122 defining an x-y plane. The top surface 122 can have a number of apertures for mounting various assemblies. A sample holder 124 is mounted on the top surface 122 of the base 120. The sample holder 124 operates to securely grip the test sample such that the specimen does not shift in position or become dislodged during crack initiation. The sample holder, as seen here, is in the form of a vise that opens horizontally.

An attachment column 140 is also mounted to the base 120. The attachment column 140 extends upward from the top surface 122 of the base 120 in a first vertical location. The attachment column 140 includes a linear rail 142 which provides free motion in the vertical direction (i.e. along a z-axis). The linear rail 142 provides a track for a carriage assembly 160.

The carriage assembly 160 includes a carriage 162 which is attached to the linear rail 142 of the attachment column 140. The carriage can slide up and down along the track of the linear rail via ball bearings (not shown) which interact with the linear rail 142. The bearings can be any suitable bearing known to those in the art, such as, for example ball bearings, dovetail bearings, linear roller bearings, magnetic or fluid bearings, etc.

The carriage assembly also includes a stage 164 that extends horizontally forwards from the linear rail 142. The stage has a first end 166 that is attached to the carriage 162 (see FIG. 3). The stage also has a second end 168 opposite the first end, or distal from the carriage 162. The stage 164 also has a top surface 170 and a bottom surface 172 extending between the two ends (see FIG. 2). The second end of the stage 164 extends over the sample holder 124, and provides a structure for supporting a razor blade holder 178 and a hammer assembly 180. The sample holder 124, razor blade holder 178, and hammer assembly 180 are located along a common second vertical axis that is spaced apart from the vertical axis occupied by the attachment column 140.

The razor blade holder 178 is attached to the bottom surface 172 of the stage 164, at the second end 168 of the stage 164. The razor blade holder is used to hold a razor blade (not visible) with the sharp end protruding downwards towards the sample holder 124 and away from the stage 164. The razor blade holder 178 can be a spring loaded clamp. The razor blade may be of any suitable size or shape. In particular embodiments, the razor blade has a straight edge. In more particular embodiments, the razor blade has a sharpness of about 30° to about 35°, as measured by the angle of the tip of the razor blade.

As seen here, the razor blade holder has a cuboid shape. A razor (not visible) is held in a slot 179 located between a first clamping portion 196 and a second clamping portion 198. A channel 199 is defined in the razor blade holder 178 roughly perpendicular to the slot, for receiving the material sample. The razor blade is contained entirely within the holder 178. The razor is securely held between the first clamping portion 196 and the second clamping portion 198 by a ball spring (not visible). To remove the razor from the razor blade holder 178, the ball spring can be disengaged to separate the first clamping portion 196 and the second clamping portion 198. The razor can then be safely removed with a pair of pliers (not shown).

Referring back to FIG. 2 and FIG. 3, the hammer assembly 180 is mounted on the top surface 170 of the stage 164, at the second end 168 of the stage 164. The hammer assembly 180 includes a vertical rod 184 extending upwards from the stage 164. An annular weighted cylinder 186 concentrically surrounds the vertical rod 184 and is operable to slide up and down the vertical rod. As shown here, the hammer assembly also includes a pipe 188 concentrically surrounding the vertical rod 184. The pipe 188 can have a first threaded end 190 and a second threaded end 192, both of which can be connected to a weighted cylinder. As seen here, the pipe 188 is connected to the annular weighted cylinder 186. Weighted cylinders can be attached to only one end or to both ends of the pipe 188. They can be used to adjust the overall weight that is being used to deliver force to the razor blade. Together, the pipe 188 and any weighted cylinders 186 can be considered an "annular weight" 182. It is noted though that the pipe is optional, and the annular weight can consist of a weighted cylinder. A ball bearing assembly (not shown) can be placed between the annular weight 182 and the vertical rod 184 to permit the annular weight to slide up and down the vertical rod.

The hammer assembly 180 can further include an adjustable stopper 194 that is attached to the vertical rod 184 above the annular weight 182. The adjustable stopper 194 is used to restrict the distance the annular weight 182 can slide up the vertical rod 184. The vertical rod 184 has scale markings at desired distances and for a desired range. For example, the vertical rod 184 can include scale markings at every 1 cm up to 20 cm. In this regard, the distance from which the weight is dropped can easily be recorded and repeated. Once fixed in place, the stopper can also be used to indicate the height at which the annular weight should be dropped, and acts as a "hard" indicator which is unambiguous and not variable (e.g. compared to visually placing the weight against a line). This provides reproducibility and consistency as to the energy of impact in repeated sample tests.

Two desirable additional aspects are visible, though it is noted that these two aspects are optional in certain embodiments. First, the drop weight tower 110 can further comprise a safety lever 146 attached to the attachment column 140. The safety lever 146 has a locked position where the lever extends into the path of the carriage assembly along the linear rail 142. This holds the carriage assembly 160 at a specified height, preventing the razor blade from falling at an undesired time. The safety lever also has an unlocked position that allows the carriage assembly 160 to move up and down the linear rail 142. The safety lever 146 may be spring loaded so that it is biased towards the locked position. The safety lever moves axially, i.e. within the x-axis, rather than about a pivot.

Second, a pillar 158 is located proximate the attachment column 140. A pneumatic cylinder 150 is mounted to the pillar. The pneumatic cylinder has a first (upper) end 152 and a second (lower) end 154, i.e. is oriented in an upwards-downwards orientation. The first end 152 is attached to the pillar 150. The second end 154 is attached to a handle 174 that extends horizontally sideways from the carriage 162. The speed of the up-down linear motion of the carriage assembly 160 along the linear rail 142 is thus controlled by the pneumatic cylinder 150. More specifically, the maximum speed of the motion of the carriage assembly 160 along the linear rail 142 can be controlled by the pneumatic cylinder 150 by adjusting the air flow through the cylinder. In this regard, at least one valve can be included in the pneumatic cylinder for adjusting the air flow. The pneumatic cylinder 150 controls the rate at which the carriage assembly 160 can be raised or lowered along the linear rail 142, such that the razor blade holder 178 can be gently brought to rest on the material sample held by the sample holder 124 and unintentional crack initiation or damage to the material sample can be prevented. This slow descent rate also acts as a safety feature for the user. The pneumatic cylinder can be a tie-rod cylinder.

The operation of the drop weight tower can be described in three steps: mounting, staging, and dropping. In the mounting step, the material sample is mounted in the sample holder and the razor blade is mounted in the razor blade holder. In the staging step, the carriage is lowered until the razor blade mounted in the razor blade holder rests on the material sample. In the dropping step, the hammer or weight is raised to a desired height and then dropped, causing the razor blade to initiate a crack in the material sample. Portions of these steps are shown in FIG. 2 and FIG. 3 (though the entire operation is not shown).

The mounting step begins with the carriage assembly 160 being elevated and held in place by the safety lever 146, so that the razor blade holder 178 is spaced apart from the sample holder 124. This can be seen in FIG. 2, where the razor blade holder 178 is above the sample holder 124, and the sample holder 124 is empty. The operation begins by mounting the material sample in the sample holder 124 and mounting the razor blade in the razor blade holder 178. The annular weight 182 is proximate the stage 164.

Next, the operation continues by releasing the safety lever 146, allowing the carriage assembly 160 to travel down the linear rail 142. The stage 164 and the hammer assembly 180 will also lower with the carriage 162. The carriage 162 is lowered until the razor blade in the razor blade holder 178 rests on the material sample. The pneumatic cylinder 150 is also used to control the rate of descent of the carriage assembly 160. It is noted that comparing FIG. 8 to FIG. 9, it can be seen that the material sample is covered by the razor blade holder 178. Put another way, the material sample enters the razor blade holder.

Next, the annular weight 182 is raised to a desired height along the vertical rod 184 until it contacts the adjustable stopper 194. This is illustrated in FIG. 2, where the annular weight 182 is raised above the top surface 170 of the stage 164. Initiating a crack in the material sample then begins by releasing the annular weight 182 from the desired height. The annular weight travels down the vertical rod 184 and forcibly impacts the top surface 170 of the stage 164. The energy of impact transfers to the razor blade holder 178, causing the razor blade to initiate a crack in the material sample.

The operation can continue by raising the carriage assembly 160 upwards along the linear rail 142 until the safety lever 146 locks the carriage in place at a specified height again, corresponding to the mounting position. The material sample can then be removed from the sample holder 124, and the razor blade can be subsequently removed from the razor blade holder 178, if desired. For safe removal of the razor blade, a specially designed wrench can be used to carry out this operation. The wrench firmly holds the razor blade and positions it centrally with the help of two protruding pins. The wrench is designed such that it fits the opening of the blade holder and helps to accurately position the razor blade in the blade holder. The operation can then be repeated with a new material sample and/or a new razor blade, if desired. Alternatively, the razor can be held in place by a ball spring as previously described.

Figure 4:
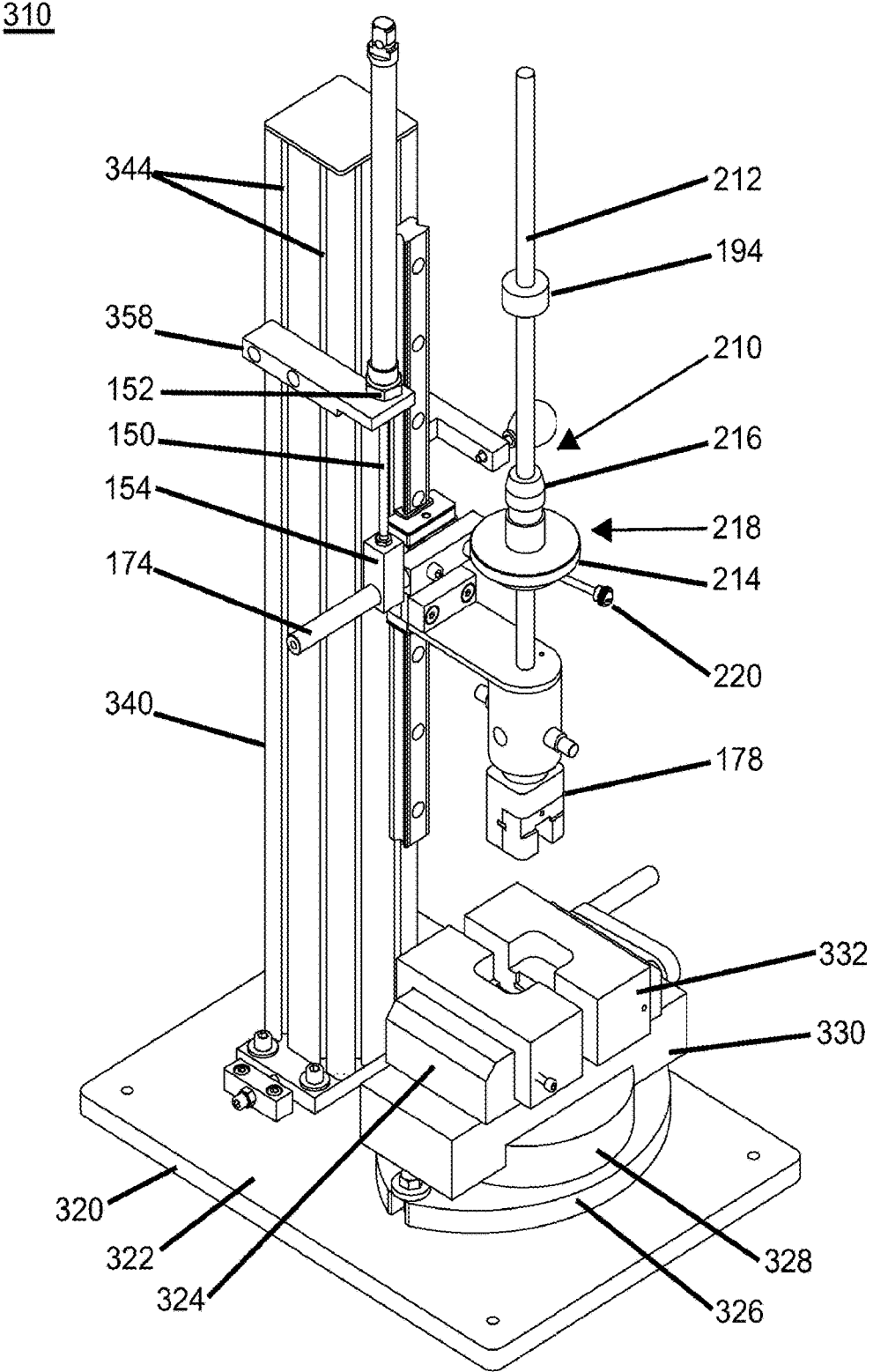
FIG. 4 is a perspective picture of a drop weight tower for crack initiation according to an additional embodiment of the present disclosure, showing the hammer assembly in a drop position.
Figure 5:
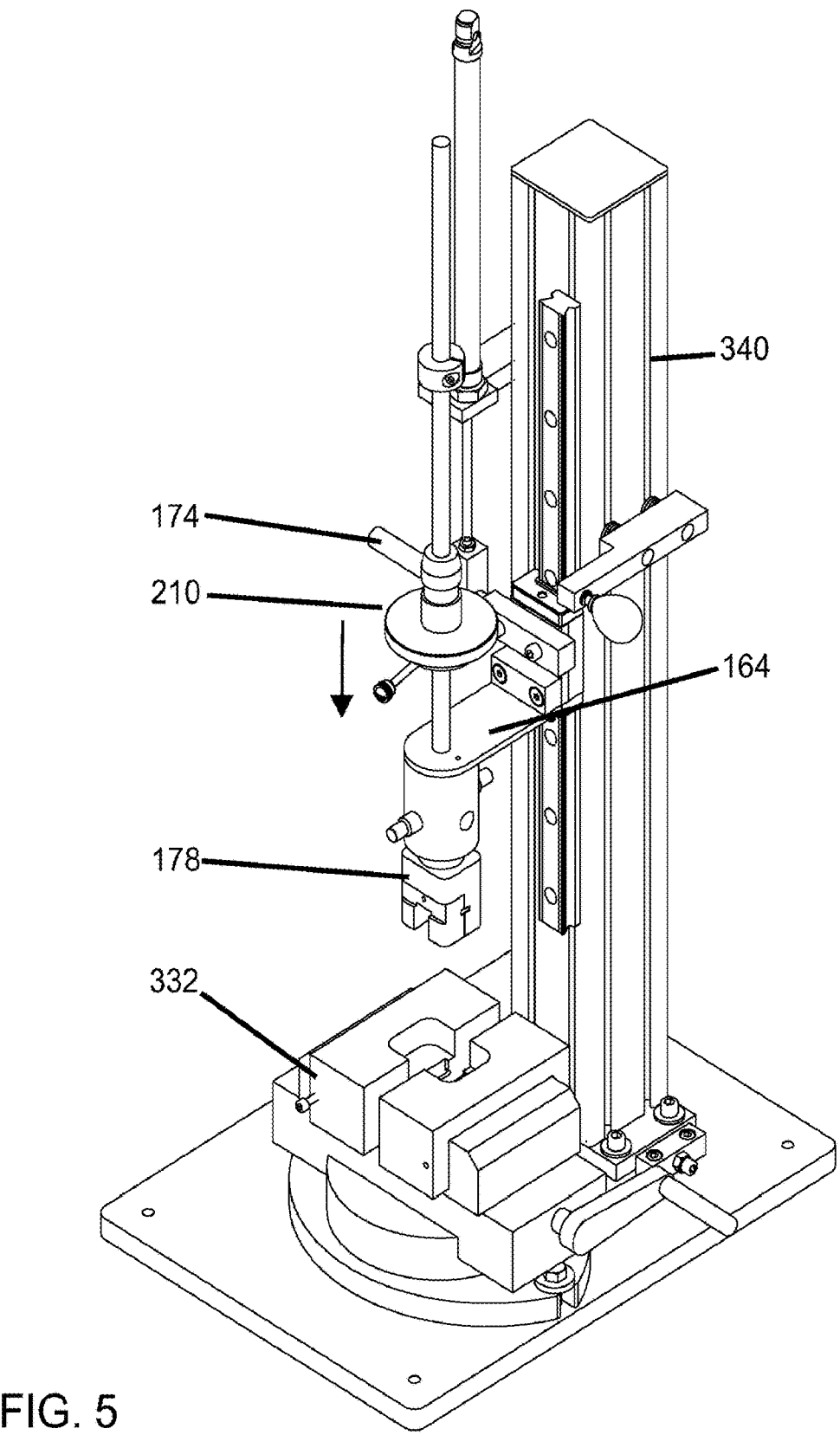
FIG. 5 is another picture of the drop weight tower of FIG. 4, from a perspective approximately 90 degrees different from that of FIG. 4.

FIG. 4 and FIG. 5 illustrate a second embodiment of a drop weight tower 310 according to the present disclosure. Some different aspects are illustrated here. As seen in FIG. 4, the hammer assembly 210 includes a vertical rod 212 extending upwards from the stage. A ball bearing assembly 216 concentrically surrounds the vertical rod 212 and is operable to smoothly slide up and down the vertical rod. An annular weighted disk 214 is connected to one end of the ball bearing assembly 216 and also concentrically surrounds the vertical rod 212. Additional weighted cylinders or discs can be placed on the ball bearing assembly 216. This can be used to adjust the overall weight that is being used to deliver force to the razor blade. Together, the ball bearing assembly 216 and any weighted disks 214 can be considered an "annular weight" 218. In FIG. 5, the hammer assembly 210 is raised above the stage 164, and the arrow indicates the downward direction that the hammer assembly will fall when the handle is released.

The annular weight 218 resting on the ball bearing assembly 216 can be easily lifted to a desired height along the vertical rod 212 via handle 220. The handle 220 is shown as being connected to the ball bearing assembly 216. However, it will be appreciated that the handle can be connected to any one of the assemblies comprising the annular weight 218 as long as the handle is operable to aid in lifting the entire annular weight.

Continuing, the drop weight tower 310 includes a base 320, which has a top surface 322 defining an x-y plane. The top surface 322 can have a number of apertures for mounting various assemblies. A sample holder 324 is mounted on top of a support pier 326 attached to and extending upward from the top surface 322 of the base 320. The support pier 326 defines a central pivot on which the sample holder 324 can rotate. A circular rim 328 on the support pier 326 defines a track or perimeter. A rim girder 330 section on the sample holder 324 can rotate around the track defined by the circular rim 328. In other words, the sample holder 324 can pivot horizontally with respect to the x-y plane of the top surface 322 to change the angle of a material sample. In this regard, the angle may need to be changed in order to ensure the sample is properly aligned with the blade. The sample holder 324 operates to securely grip a positioning fixture 332 that holds the material sample in place such that it does not shift in position or become dislodged during crack initiation. The sample holder, as seen here, is in the form of a vise that opens horizontally.

Figure 6:
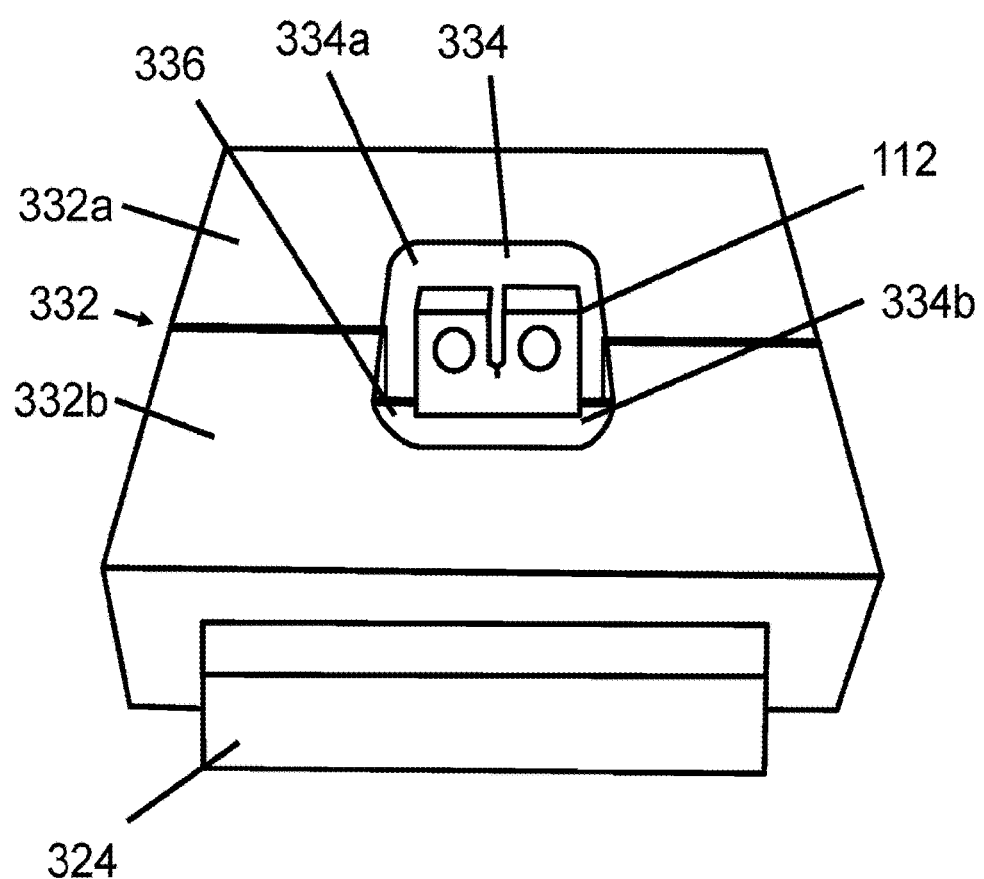
FIG. 6 is a perspective view of the positioning fixture used in the embodiment of FIG. 4.

As seen in FIG. 6, the positioning fixture 332 comprises a first positioning block 332a and a second positioning block 332b. A cavity 334 is defined in a central portion of the positioning fixture 332. The cavity 334 comprises a first cavity section 334a defined in the first positioning block 332a and a second cavity section 334b defined in the second positioning block 332b. A bottom surface 336 of the cavity is adapted to support the material sample 112 within the positioning fixture 332. In this manner, the material sample is aligned with the blade. The first cavity section 334a and second cavity section 334b are also sized such that the razor blade holder 178 (see FIG. 5) fits directly into the cavity 334.

The razor blade holder 178 is shown as having a cuboid shape, thus the cavity 334 of the positioning fixture 332 also has a cuboid shape. However, it is contemplated that the cavity 334 can have any shape sized to fit the shape of the razor blade holder and/or the size of the material sample. In this regard, positioning fixtures having cavities with different shapes can easily be switched out to match the size and shape of the razor blade holder and/or material sample being used. This advantageously saves time by not having to re-align each new material sample for testing.

Referring back to FIG. 4 and FIG. 5, an attachment column 340 is also mounted to the base 320. The attachment column 340 extends upward from the top surface 322 of the base 320 in a first vertical location. The attachment column 340 includes one or more attachment features such as channels 344. A support cantilever 358 is mounted to the attachment features 344 and is adapted to secure the pneumatic cylinder 150. The support cantilever 358 extends outward from the attachment column 340 in order to proximately mount the pneumatic cylinder 150 to the attachment column. The first (upper) end 152 of the pneumatic cylinder 150 is attached to the support cantilever 358. The second (lower) end 154 of the pneumatic cylinder 150 is attached to the handle 174.

As will be appreciated by the description of the aforementioned embodiments, the operation of the drop weight tower can also include adjusting the impact energy of the weight being dropped on the top surface of the stage. One method of adjusting the impact energy can include raising or lowering the adjustable stopper 194 to increase or decrease the height from which the annular weight 182 or annular weight 218 can be released. Another method can include adjusting the weight of the annular weight. This can be accomplished by including the optional pipe 188, to which additional weights can be added via the first threaded end 190 and second threaded end 192. Alternatively, a heavier weight can be provided. This can also be accomplished by adding more weighted discs 214 to the ball bearing assembly 216.

Figure 9:
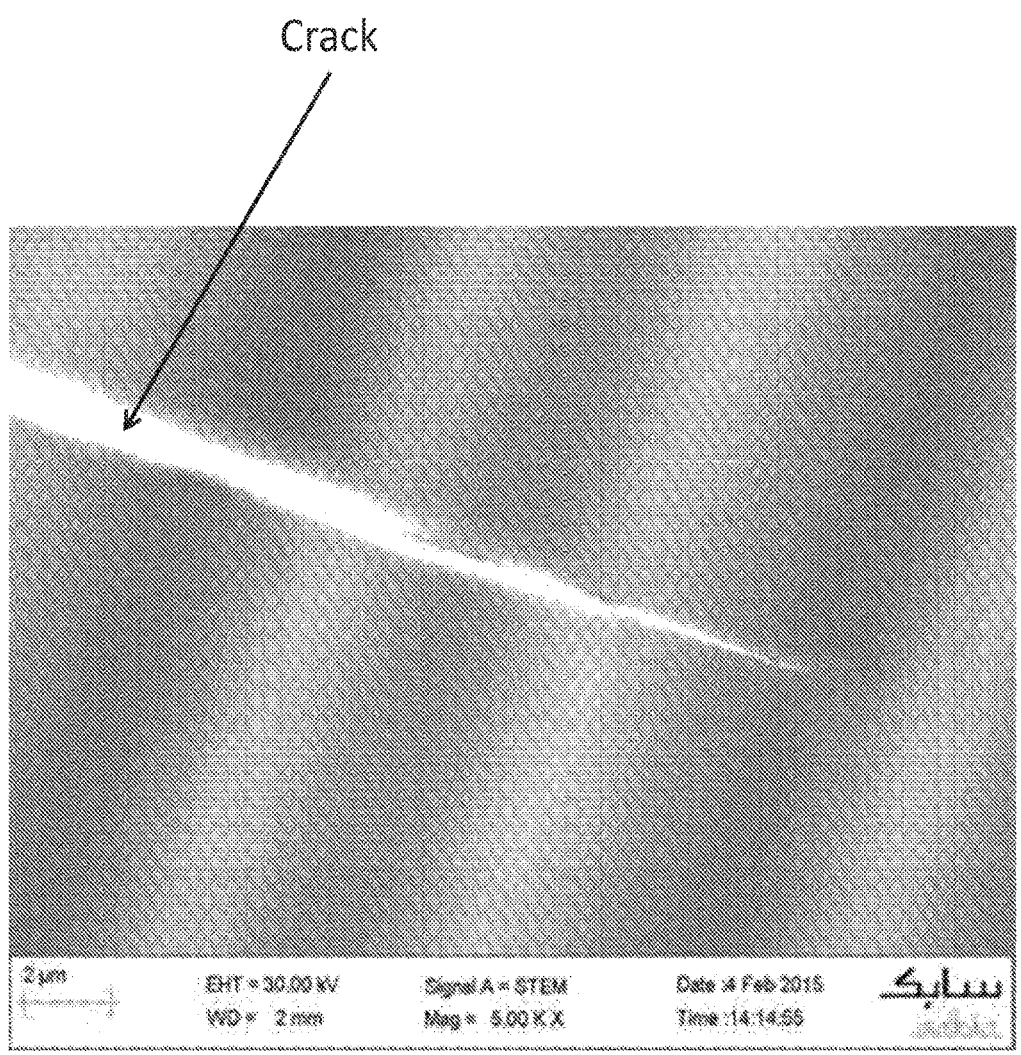
FIG. 9 is a scanning transmission electron microscopy (STEM) picture of a typical crack produced by the drop weight tower in an epoxy material, showing the sharpness of the crack.
Figure 10:
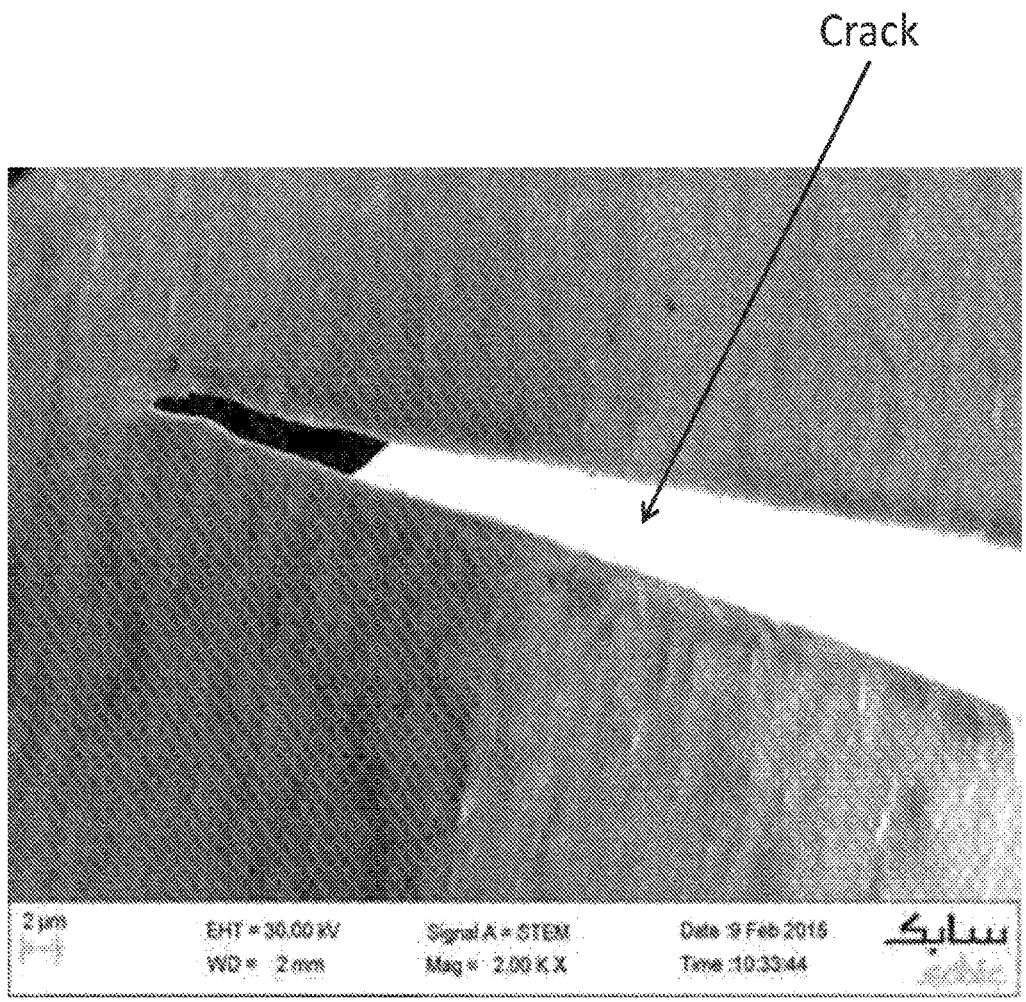
FIG. 10 is a scanning transmission electron microscopy (STEM) picture of a typical crack produced by the drop weight tower in a thermoplastic material (polybutylene terephthalate, PBT).

The drop weight tower is useful in testing both thermoset polymers and engineering thermoplastic polymers. Thermoset polymers can be brittle, and the drop weight tower produces consistently sharp cracks, as seen in FIG. 9. Thermoplastic polymers are generally ductile, and the drop weight tower will produce consistently sharp notches therein, as seen in FIG. 10.

The following examples are provided to illustrate the devices and methods of the present disclosure. The examples are merely illustrative and are not intended to limit the disclosure to the materials, conditions, or process parameters set forth therein.

EXAMPLE 1

Figure 7:
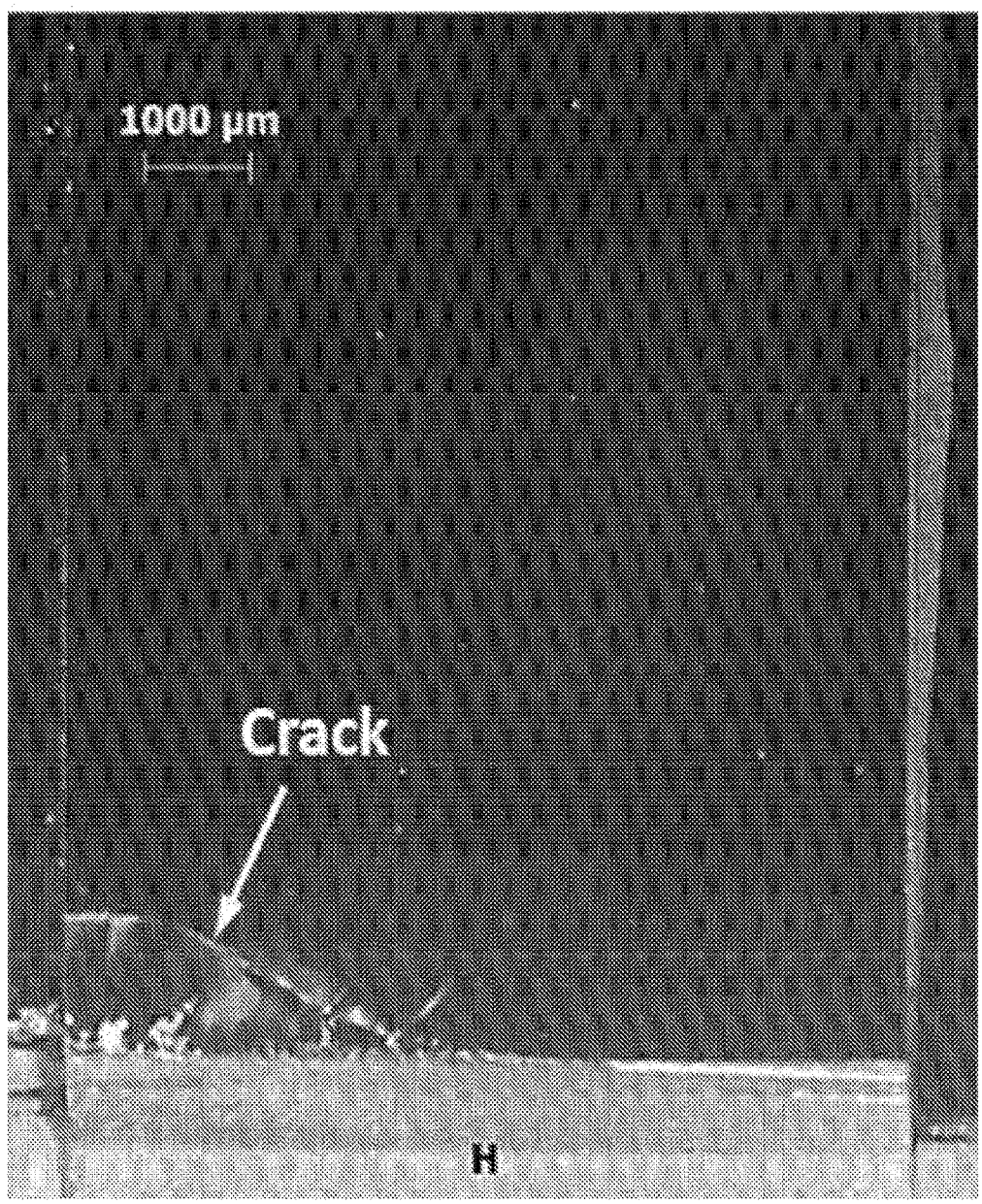
FIG. 7 is a picture of a typical crack produced by a conventional manual razor tap method, showing a crack which is non-uniform across the thickness of the sample.
Figure 8:
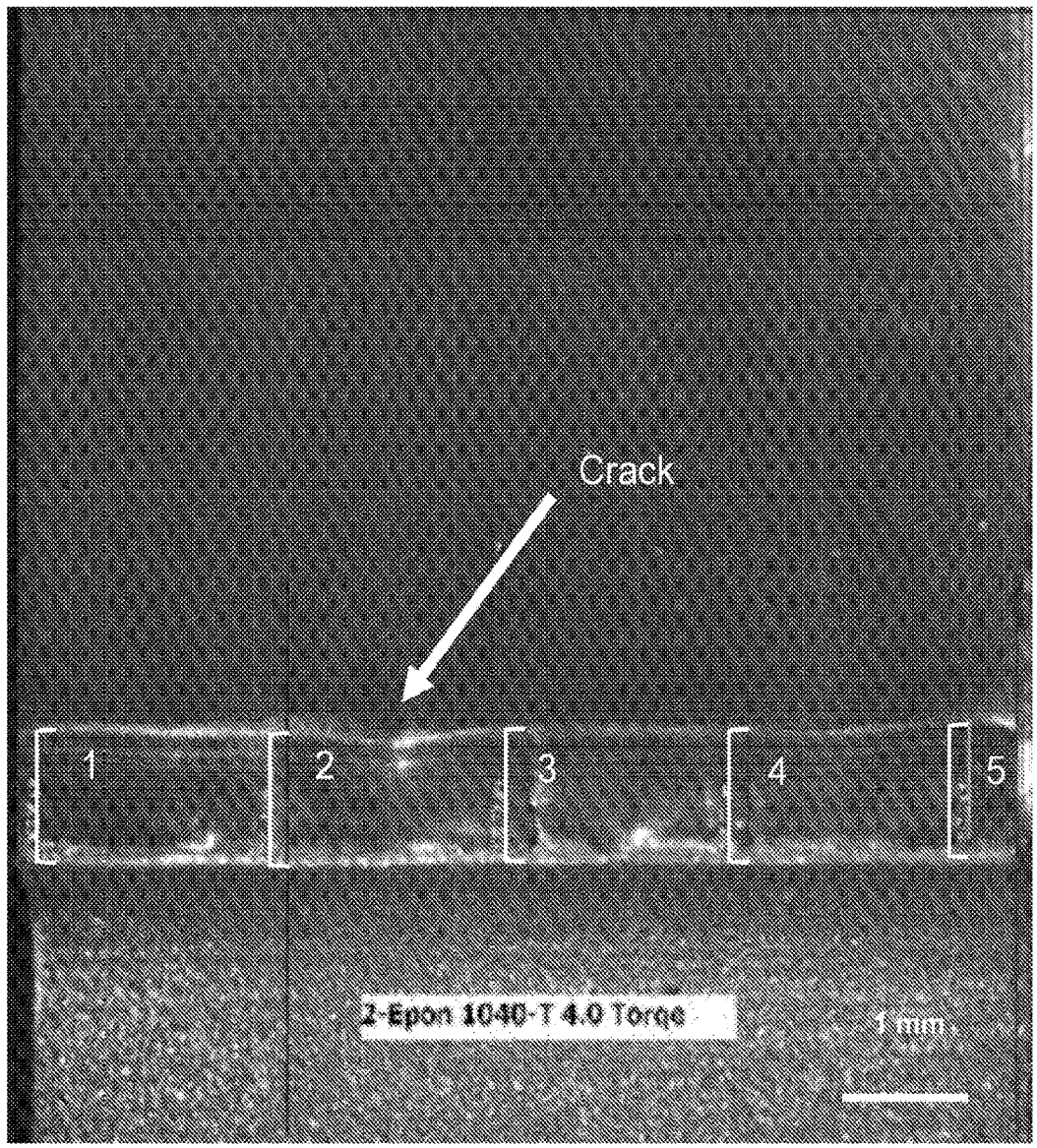
FIG. 8 is a picture of a typical crack produced by the drop weight tower of FIG. 4 and FIG. 5, showing a crack which is relatively uniform across the thickness of the sample. Five measurements were made on the fracture surface of samples at equal intervals.

A preliminary analysis was performed to compare a traditional razor tap method with the drop weight tower according to the embodiments disclosed herein for crack initiation in fracture mechanics samples. A total of 28 epoxy material samples were made. Samples were casted in negative silicone mold in compact tension geometry, as illustrated in FIG. 1. The samples were divided into 2 equal groups (N=14/group) and labeled A-N. In one group, a crack was initiated using the traditional razor tap method. In the other group, a crack was initiated using the drop weight tower depicted in FIG. 2 and FIG. 3. The drop weight tower was operated as described above. The annular weight 182 was approximately 527 grams and was dropped from 5 centimeter height. A small hammer of comparable weight was used for the traditional razor tap method. An upper set limit for crack length was designated at 1 millimeter, and lower set limit was designated at 0.25 millimeter. The upper and lower limits were set to achieve a crack length (a) over specimen width (W) ratio (a/W) between 0.45 and 0.55, according to ASTM D5045. The cracked samples were loaded in a universal test machine and cracks were catastrophically extended. The broken samples were then imaged under an optical microscope to measure the crack length prepared by the two methods. The crack lengths were measured at five equal intervals on the fracture surface, as shown in FIG. 8 and averaged to obtain an average crack length for each sample. The load at failure was recorded and used along with the sample geometry and the average crack length to calculate the fracture toughness ($K_{1c}$) for the epoxy material according to ASTM D5045. The critical strain energy release rate ($G_{1c}$) was also calculated for the epoxy material. Pictures of cracks produced by the razor tap method and produced by the drop weight tower are shown in FIG. 7 and FIG. 8, respectively. A significant difference in the uniformity for crack length, critical strain energy release rate, and fracture toughness between the two methods, is shown in Table 1 and 2 below, and in FIG. 11 and FIG. 12.

TABLE 1

Crack Initiation Results with Razor Tap Method

| Spec-imen | Crack Length in mm | | | | | Average (mm) | $G_{IC}$ (J/m²) | $K_{IC}$ MPa√m | Notes |
|---|---|---|---|---|---|---|---|---|---|
| | 1 | 2 | 3 | 4 | 5 | | | | |
| A | 0.00 | 0.00 | 0.00 | 0.00 | 0.00 | 0.00 | 2106 | 2.09 | No Crack |
| B | 0.00 | 0.00 | 0.67 | 1.90 | 1.65 | 0.85 | 217 | 0.68 | |
| C | 0.95 | 0.54 | 0.00 | 0.00 | 0.00 | 0.30 | 412 | 0.92 | |
| D | 0.00 | 0.00 | 0.00 | 0.00 | 0.00 | 0.00 | 3502 | 2.78 | No Crack |
| E | 0.24 | 0.22 | 0.24 | 0.25 | 0.33 | 0.25 | 291 | 0.72 | |
| F | 0.00 | 0.00 | 0.00 | 0.00 | 0.00 | 0.00 | | | No Crack |
| G | 0.00 | 0.00 | 0.00 | 0.00 | 0.25 | 0.05 | 1203 | 1.56 | |
| H | 1.18 | 0.89 | 0.00 | 0.00 | 0.00 | 0.41 | 419 | 0.92 | |
| I | 0.00 | 0.00 | 0.16 | 0.34 | 0.51 | 0.20 | 1344 | 1.66 | |
| J | 0.86 | 0.56 | 0.27 | 0.15 | 0.33 | 0.43 | 319 | 0.79 | |
| K | 0.00 | 0.00 | 0.00 | 0.13 | 0.26 | 0.08 | 1534 | 1.78 | |
| L | 0.00 | 0.18 | 0.33 | 0.52 | 0.51 | 0.31 | 1946 | 2.09 | |
| M | 0.47 | 0.53 | 0.83 | 0.33 | 0.32 | 0.50 | 268 | 0.76 | |
| N | 0.00 | 0.00 | 0.00 | 0.00 | 1.12 | 0.22 | 521 | 0.99 | |

TABLE 2

Crack Initiation Results with Drop Weight Tower of FIG. 2

| Spec-imen | Crack Length in mm | | | | | Average (mm) | $G_{IC}$ (J/m²) | $K_{IC}$ MPa√m | Notes |
|---|---|---|---|---|---|---|---|---|---|
| | 1 | 2 | 3 | 4 | 5 | | | | |
| A | 0.00 | 0.15 | 0.54 | 1.22 | 1.12 | 0.61 | 274 | 0.70 | |
| B | 0.36 | 0.33 | 0.44 | 0.46 | 0.34 | 0.39 | 271 | 0.71 | |
| C | 0.63 | 0.73 | 0.62 | 0.36 | 0.13 | 0.49 | 201 | 0.65 | |
| D | 0.36 | 0.45 | 0.49 | 0.51 | 0.38 | 0.44 | 317 | 0.77 | |
| E | 0.13 | 0.25 | 0.38 | 0.39 | 0.58 | 0.35 | 391 | 0.86 | |
| F | 0.53 | 0.49 | 0.25 | 0.16 | 0.15 | 0.32 | 282 | 0.69 | |
| G | 0.69 | 0.74 | 0.41 | 0.18 | 0.00 | 0.41 | 226 | 0.65 | |
| H | 0.05 | 0.27 | 0.31 | 0.34 | 0.38 | 0.27 | 340 | 0.75 | |
| I | 0.69 | 0.82 | 0.73 | 0.54 | 0.36 | 0.63 | 202 | 0.64 | |
| J | 0.58 | 0.49 | 0.38 | 0.25 | 0.29 | 0.40 | 287 | 0.79 | |
| K | 0.44 | 0.69 | 0.44 | 0.27 | 0.11 | 0.39 | 259 | 0.73 | |
| L | 0.34 | 0.91 | 0.54 | 0.22 | 0.09 | 0.42 | 242 | 0.68 | |
| M | 0.27 | 0.46 | 0.46 | 0.38 | 0.38 | 0.39 | 432 | 0.84 | |
| N | 0.49 | 0.40 | 0.29 | 0.09 | 0.00 | 0.25 | 288 | 0.69 | |

Figure 11:
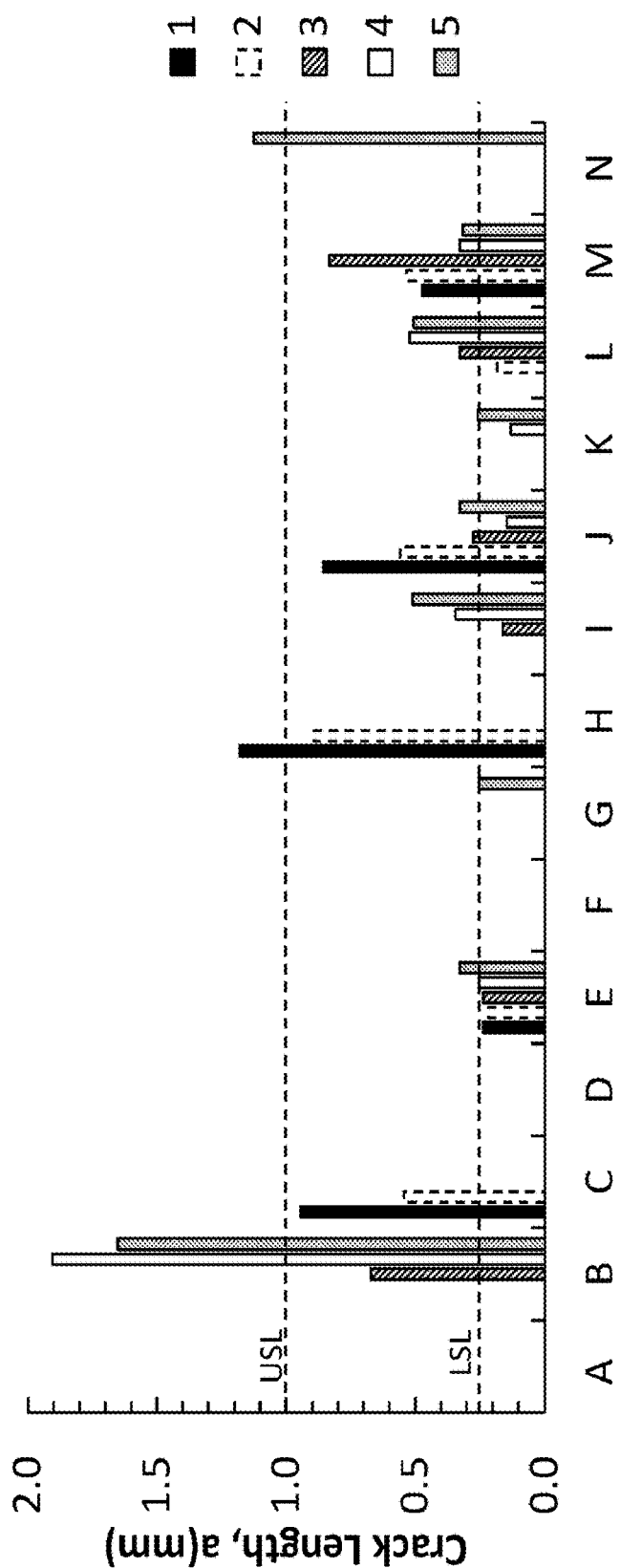
FIG. 11 is a chart showing the crack lengths obtained on samples using a manual drop method. Five measurements were made on the fracture surface of samples at equal intervals, as shown in FIG. 8. The desired lower specification limit (LSL) and upper specification limit (USL) were 0.25 mm and 1.0 mm, respectively.
Figure 12:
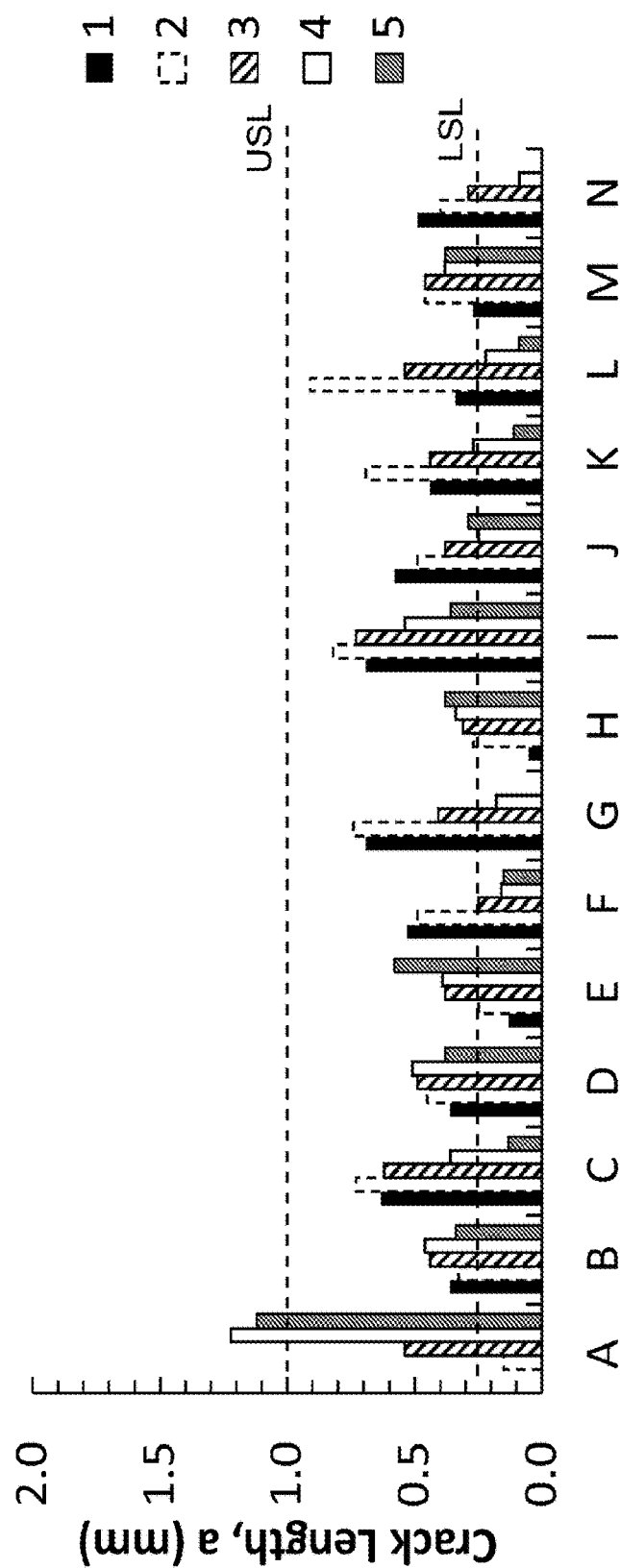
FIG. 12 is a chart showing the crack lengths obtained on samples using the drop weight tower of FIG. 2 and FIG. 3.

In Tables 1 and 2, crack length values are in millimeters and fracture toughness values are in MPa·m$^{0.5}$. The results for specimens A-N from Table 1 are also shown in the graph of FIG. 11. The results for specimens A-N from Table 2 are similarly shown in the graph of FIG. 12. In FIG. 11 and FIG. 12, the upper dotted line designated USL represents an upper set limit for crack length of 1 millimeter and the lower dotted line designated LSL represents a lower set limit for crack length of 0.25 millimeter. Desirably, all values should fall between these two set limits, which would demonstrate consistency, repeatability, and reproducibility of the process.

As shown in Table 1 and FIG. 11, the manual razor tap method resulted in the majority of samples having a length that was outside of the two set limits. There was also considerable variation between the crack lengths on each sample. In other words, the results in Table 1 and FIG. 11 demonstrated the difficulty in performing the manual razor tap method in a repeatable and reproducible manner. Note that no crack initiation was achieved in three samples A, D, and F, as the operator did not apply sufficient impact energy to initiate a crack. Out of the three samples, sample F did not generate toughness data due to an equipment malfunction and therefore was not included in the toughness analysis.

In contrast, Table 2 and FIG. 12 show that the drop weight tower initiated cracks in all 14 samples and the samples had more values within the two set limits. In addition, there was less variation between the crack lengths on each sample. This resulted in less variation between the $K_{1c}$ and $G_{1c}$ values compared to the manual razor tap method. Thus, the results in Table 2 and FIG. 12 demonstrate that the drop weight tower provided more consistent, repeatable, and reproducible conditions for fracture mechanics testing compared to the manual method.

One way ANOVA showed a significant difference in the process mean for crack length and fracture toughness between the two methods, as shown in Table 3 and 4 below.

In Table 3, crack length values are in millimeters. In Table 4, fracture toughness values are in MPa·m$^{0.5}$. Table 3 shows that the drop weight tower significantly (p<0.05) improved the mean crack length. Also, Table 4 shows that the fracture toughness ($K_{1c}$) of the epoxy material as determined by the two methods are significantly different. In other words, the drop weight tower demonstrated repeatable and consistent $K_{1c}$ values versus the manual method. In addition, the overall uniformity and sharpness of a crack across the sample thickness can also be improved.

FIG. 9 is a picture of a typical crack produced in an epoxy material. The epoxy material was 100 parts Epon 828 (an undiluted clear difunctional bisphenol A/epichlorohydrin derived liquid epoxy resin), 5 phr Ultem® 1040 (a polyetherimide) with respect to the epoxy, and 30 phr 4,4-diaminodiphenylsulfone with respect to the epoxy. The crack is very sharp with the crack tip radius in tens of nanometers. Similarly, FIG. 10 is a picture of a typical notch produced in a thermoplastic material, which is also sharp with crack tip radius in hundreds of nanometer. The thermoplastic material was polybutylene terephthalate (PBT).

TABLE 3

One-way ANOVA: Manual Method, Drop Weight Tower

| Method | |
|---|---|
| Null hypothesis | All means are equal |
| Alternative hypothesis | At least one mean is different |
| Significance level | α = 0.05 |

Equal variances were assumed for the analysis.

TABLE 3-continued

Factor Information

| Factor | Levels | Values |
|---|---|---|
| Factor | 2 | Manual Method, Drop Weight Tower |

Analysis of Variance

| Source | DF | Adj SS | Adj MS | F-Value | P-Value |
|---|---|---|---|---|---|
| Factor | 1 | 0.1628 | 0.16276 | 4.74 | 0.039 |
| Error | 26 | 0.8924 | 0.03432 | | |
| Total | 27 | 1.0551 | | | |

Model Summary

| S | R-sq | R-sq (adj) | R-sq (pred) |
|---|---|---|---|
| 0.185263 | 15.43% | 12.17% | 1.91% |

Means

| Factor | N | Mean | StDev | 95% CI |
|---|---|---|---|---|
| Manual Method | 14 | 0.2575 | 0.2387 | (0.1558, 0.3593) |
| Drop Weight Tower | 14 | 0.4100 | 0.1080 | (0.3082, 0.5118) |

Pooled StDev = 0.185263

TABLE 4

One-way ANOVA: Manual Method, Razor Tap Method

Method

| | |
|---|---|
| Null hypothesis | All means are equal |
| Alternative hypothesis | At least one mean is different |
| Significance level | $\alpha = 0.05$ |
| Rows unused | 1 |

Equal variances were assumed for the analysis.

Factor Information

| Factor | Levels | Values |
|---|---|---|
| Factor | 2 | Manual Method, Drop Weight Method |

Analysis of Variance

| Source | DF | Adj SS | Adj MS | F-Value | P-Value |
|---|---|---|---|---|---|
| Factor | 1 | 2.758 | 2.7577 1 | 2.46 | 0.002 |
| Error | 25 | 5.531 | 0.2213 | | |
| Total | 26 | 8.289 | | | |

Model Summary

| S | R-sq | R-sq (adj) | R-sq (pred) |
|---|---|---|---|
| 0.470382 | 33.27% | 30.60% | 21.69% |

Means

| Factor | N | Mean | StDev | 95% CI |
|---|---|---|---|---|
| Manual Method | 13 | 1.365 | 0.675 | (1.096, 1.633) |
| Drop Weight Tower | 14 | 0.7250 | 0.0691 | (0.4661, 0.9839) |

Pooled StDev = 0.470382

In summary, the drop weight tower advantageously permits repeatable and reproducible test conditions that achieve consistent crack lengths in samples used for fracture mechanics testing. This is demonstrated in Table 2 and FIG. 12. These results would otherwise be difficult to achieve using a traditional razor tap method.

EXAMPLE 2

A second analysis was performed to compare a traditional razor tap method with the drop weight tower according to another embodiment disclosed herein for crack initiation in fracture mechanics samples. A total of 20 epoxy material samples were made. Samples were casted in negative silicone mold in compact tension geometry, as illustrated in FIG. 1. The samples were divided into 2 equal groups (N=10/group) and labeled A-J. In one group, a crack was initiated using the traditional razor tap method.

In another group, a crack was initiated using the drop weight tower depicted in FIG. 4 and FIG. 5. A picture of cracks in a sample produced by the drop weight tower depicted in FIG. 4 and FIG. 5 is shown in FIG. 8. The drop weight tower was operated as described above. An upper set limit for crack length was designated at 1 millimeter, and lower set limit was designated at 0.25 millimeter.

The cracked samples were loaded in a universal test machine and cracks were catastrophically extended. The broken samples were then imaged under an optical microscope to measure the crack length prepared by the two methods. The crack lengths were measured at five equal intervals on the fracture surface, as shown in FIG. 8 and averaged to obtain an average crack length for each sample. The load at failure was recorded and used along with the sample geometry and crack length to calculate the fracture toughness ($K_{1c}$) for the epoxy material according to ASTM D5045. The critical strain energy release rate ($G_{1c}$) was also calculated for the epoxy material. A significant difference in the uniformity for crack length, critical strain energy release rate, and fracture toughness between the two methods, is shown in Table 5 and 6 below, and in FIG. 13 and FIG. 14.

TABLE 5

Crack Initiation Results with Razor Tap Method

| | Crack Length in mm | | | | | Average | $G_{IC}$ | $K_{IC}$ | |
|---|---|---|---|---|---|---|---|---|---|
| Specimen | 1 | 2 | 3 | 4 | 5 | (mm) | (J/m²) | MPa√m | Notes |
| A | 8.84 | 9.91 | 10.42 | 10.20 | 9.47 | 19.77 | 0 | 0.00 | Broke |
| B | 0.76 | 0.42 | 1.28 | 1.71 | 1.77 | 1.19 | 336 | 0.77 | |
| C | 1.19 | 1.45 | 1.44 | 1.01 | 0.94 | 1.21 | 338 | 0.80 | |
| D | 11.61 | 12.31 | 12.62 | 12.76 | 12.89 | 20.77 | 0 | 0.00 | Broke |
| E | 1.26 | 1.29 | 1.36 | 1.27 | 1.37 | 1.31 | 259 | 0.68 | |
| F | 0.00 | 0.00 | 0.22 | 0.40 | 0.51 | 0.38 | 1239 | 1.55 | |
| G | 1.51 | 1.24 | 0.84 | 0.57 | 0.00 | 1.04 | 340 | 0.78 | |

TABLE 5-continued

Crack Initiation Results with Razor Tap Method

| Specimen | Crack Length in mm | | | | | Average (mm) | $G_{IC}$ (J/m$^2$) | $K_{IC}$ MPa√m | Notes |
|---|---|---|---|---|---|---|---|---|---|
| | 1 | 2 | 3 | 4 | 5 | | | | |
| H | 0.00 | 0.08 | 0.41 | 0.99 | 1.42 | 0.72 | 512 | 0.98 | |
| I | 1.12 | 1.58 | 2.42 | 3.30 | 3.31 | 2.35 | 348 | 0.79 | |
| J | 10.14 | 10.93 | 11.27 | 11.04 | 10.46 | 20.77 | 0 | 0.00 | Broke |

TABLE 6

Crack Initiation Results with Drop Weight Tower of FIG. 4

| Specimen | Crack Length in mm | | | | | Average (mm) | $G_{IC}$ (J/m$^2$) | $K_{IC}$ MPa√m | Notes |
|---|---|---|---|---|---|---|---|---|---|
| | 1 | 2 | 3 | 4 | 5 | | | | |
| A | 0.77 | 0.70 | 0.74 | 0.79 | 0.82 | 0.76 | 334 | 0.72 | |
| B | 0.87 | 0.78 | 0.66 | 0.56 | 0.55 | 0.69 | 305 | 0.71 | |
| C | 0.93 | 0.79 | 0.71 | 0.66 | 0.65 | 0.75 | 331 | 0.76 | |
| D | 0.49 | 0.47 | 0.56 | 0.49 | 0.60 | 0.52 | 350 | 0.77 | |
| E | 0.86 | 0.73 | 0.67 | 0.61 | 0.64 | 0.70 | 304 | 0.75 | |
| F | 0.72 | 0.59 | 0.57 | 0.55 | 0.63 | 0.61 | 320 | 0.75 | |
| G | 0.72 | 0.60 | 0.57 | 0.54 | 0.54 | 0.60 | 390 | 0.78 | |
| H | 0.57 | 0.54 | 0.57 | 0.63 | 0.63 | 0.59 | 305 | 0.73 | |
| I | 0.55 | 0.54 | 0.59 | 0.59 | 0.69 | 0.59 | 315 | 0.75 | |
| J | 0.75 | 0.72 | 0.83 | 0.89 | 0.90 | 0.82 | 330 | 0.75 | |

Figure 13:
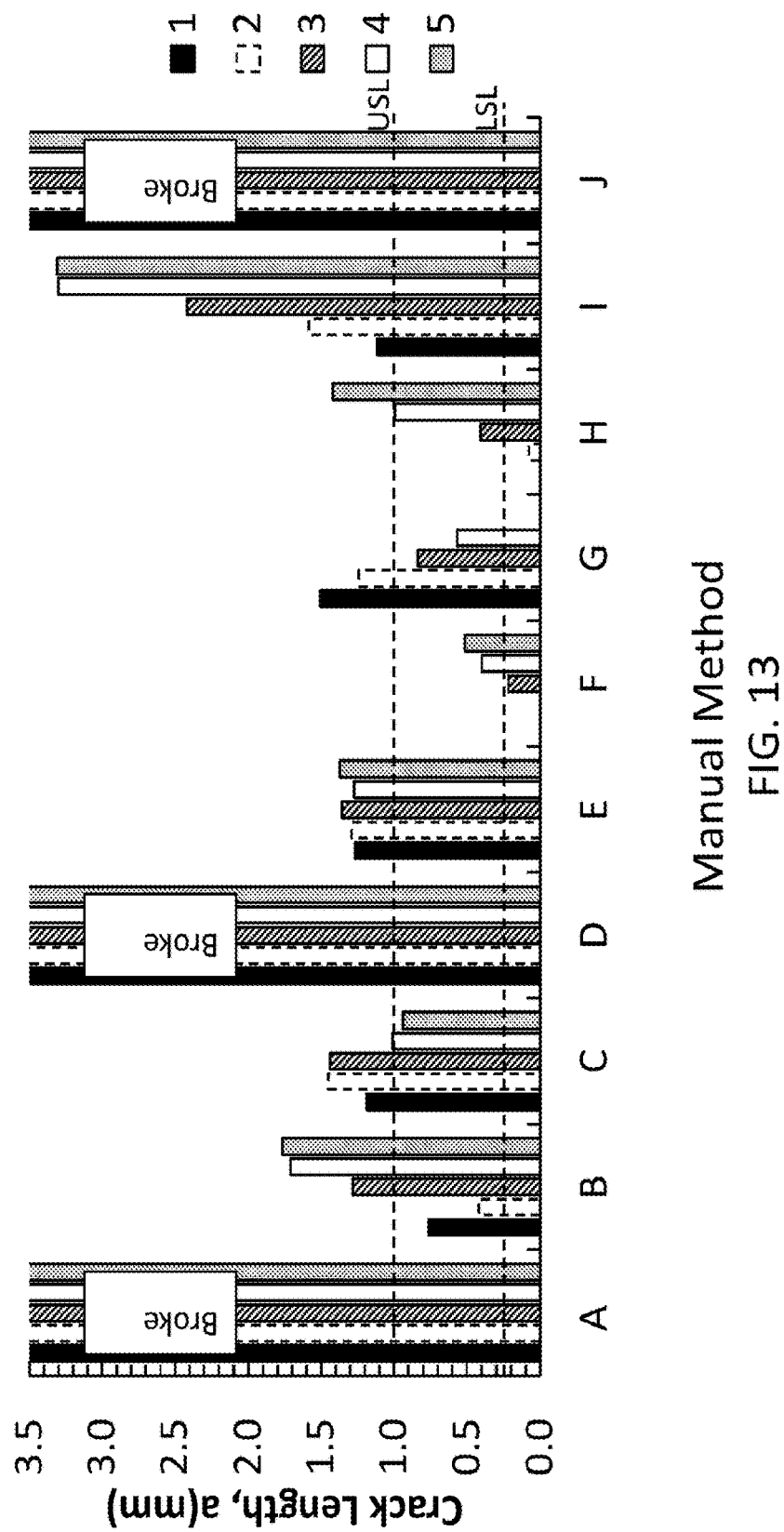
FIG. 13 is a chart showing the crack lengths obtained on another set of samples using a manual drop method.
Figure 14:
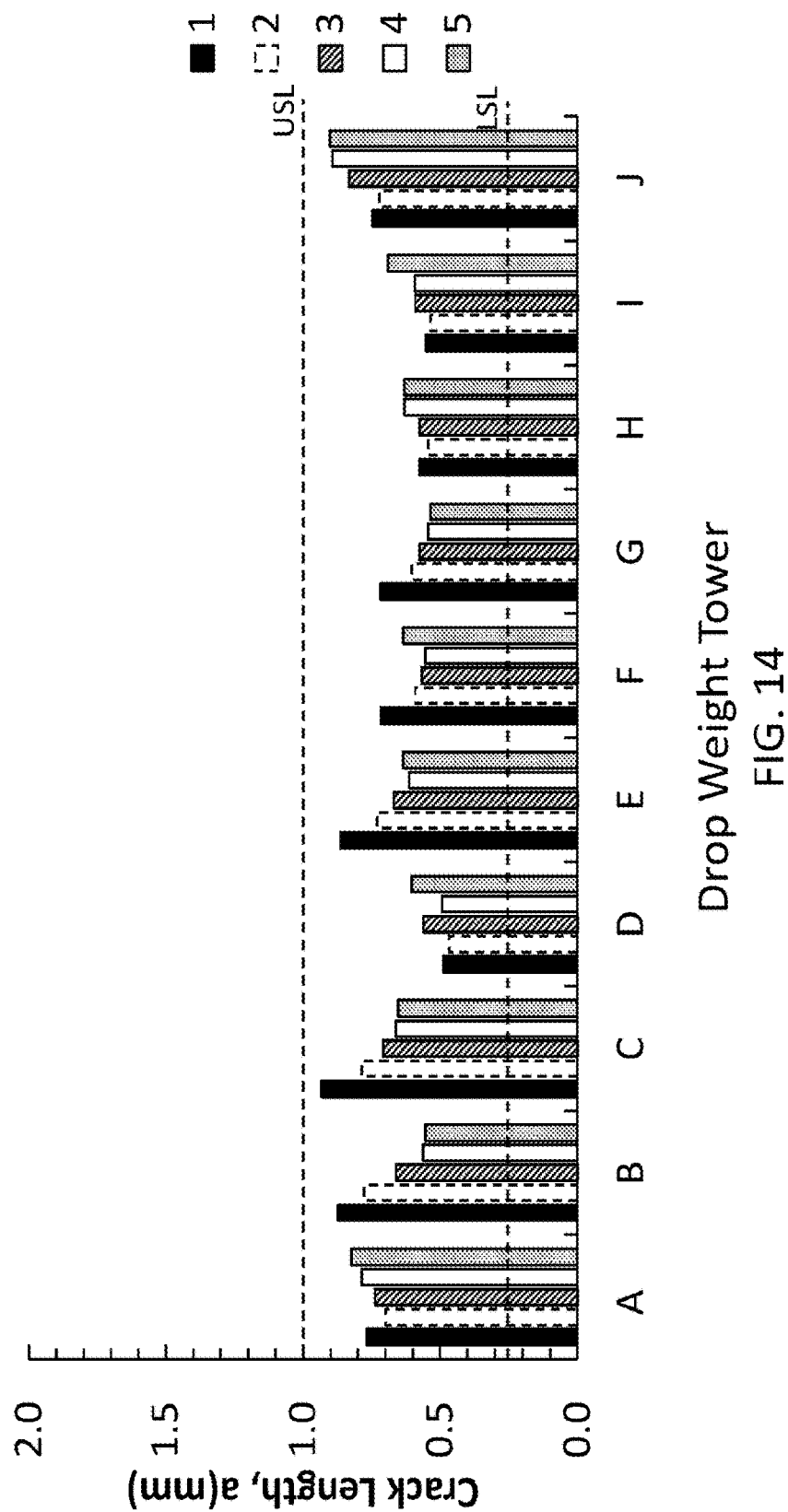
FIG. 14 is a chart showing the crack lengths obtained on samples using the drop weight tower of FIG. 4 and FIG. 5.

In Tables 5 and 6, crack length values are in millimeters and fracture toughness values are in MPa·m$^{0.5}$. The results from Table 5 are also shown in the graph of FIG. 13. The results from Table 6 are similarly shown in the graph of FIG. 14. In FIG. 13 and FIG. 14, the upper dotted line designated USL represents an upper set limit for crack length of 1 millimeter and the lower dotted line designated LSL represents a lower set limit for crack length of 0.25 millimeter. Again, desirably all values should fall between these two set limits.

As shown in Table 5 and FIG. 13, the majority of samples made using the manual razor tap method had values outside of the two set limits. Again, there was considerable difficulty in reliably reproducing crack lengths. Three of the samples A, D, and J broke and therefore no fracture toughness data was obtained.

In contrast, Table 6 and FIG. 14 show that the drop weight tower initiated cracks in the samples whose lengths were consistently within the two set limits. In addition, there was much less variation between the crack lengths on each sample. Here, all of the crack lengths were within the two set limits. This consistency is shown in the picture of FIG. 8, where a crack was initiated using the drop weight tower shown in FIG. 4 and FIG. 5. As can be seen in FIG. 8, crack lengths 1-5 are consistent across the sample thickness.

One way ANOVA showed a significant difference in the process mean for crack length and standard deviation for fracture toughness between the two methods, as shown in Table 7 and 8 below.

TABLE 7

One-way ANOVA: Manual Method, Drop Weight Tower

Method

| Null hypothesis | All means are equal |
|---|---|
| Alternative hypothesis | At least one mean is different |
| Significance level | α = 0.05 |

Equal variances were assumed for the analysis.

TABLE 7-continued

Factor Information

| Factor | Levels | Values | | |
|---|---|---|---|---|
| Factor | 2 | Manual Method, Drop Weight Tower | | |

Analysis of Variance

| Source | DF | Adj SS | Adj MS | F-Value | P-Value |
|---|---|---|---|---|---|
| Factor | 1 | 197.7 | 197.70 | 4.55 | 0.047 |
| Error | 18 | 782.4 | 43.47 | | |
| Total | 19 | 980.1 | | | |

Model Summary

| S | R-sq | R-sq (adj) | R-sq (pred) |
|---|---|---|---|
| 6.59300 | 20.17% | 15.74% | 1.45% |

Means

| Factor | N | Mean | StDev | 95% CI |
|---|---|---|---|---|
| Manual Method | 10 | 6.95 | 9.32 | (2.57, 11.33) |
| Drop Weight Tower | 10 | 0.6629 | 0.0948 | (−3.7173, 5.0431) |

Pooled StDev = 6.59300

TABLE 8

One-way ANOVA: Manual Method, Drop Weight Tower

Method

| Null hypothesis | All variances are equal |
|---|---|
| Alternative hypothesis | At least one variance is different |
| Significance level | α = 0.05 |

F method is used. This method is accurate for normal data only.
95% Bonferroni Confidence Intervals for Standard Deviations

| Sample | N | StDev | CI |
|---|---|---|---|
| Manual Method | 7 | 0.297305 | (0.180686, 0.747875) |
| Drop Weight Tower | 10 | 0.021628 | (0.014147, 0.043552) |

Individual confidence level = 97.5%

Tests

| Method | Test Statistic | P-Value |
|---|---|---|
| F | 188.96 | 0.000 |

Comparing FIG. 14 to the results of FIG. 12 (the drop weight tower of FIG. 2), the consistency and repeatability is also markedly improved. This is seen in FIG. 14 and Table 8 in both the lower variation between crack lengths on each sample, and in the fact that all crack lengths are within the two set limits.

TABLE 9

Process capability analysis based on average crack length

| Statistics | Manual Method | Drop Weight Tower (FIGS. 2-3) | Drop Weight Tower (FIGS. 4-5) |
|---|---|---|---|
| % Out of Spec | 48.84 | 6.91 | 0.02 |
| PPM (DPMO) | 488357 | 69142 | 196 |

In summary, the drop weight tower advantageously permits repeatable and reproducible test conditions that achieve consistent crack lengths in samples used for fracture mechanics testing. This is demonstrated in Table 6 and FIG. 14. These results would otherwise be difficult to achieve using a traditional razor tap method.

The present disclosure has been described with reference to exemplary embodiments. Obviously, modifications and alternations will occur to others upon reading and understanding the preceding detailed description. It is intended that the present disclosure be construed as including all such modifications and alterations insofar as they come within the scope of the appended claims or the equivalents thereof.

The invention claimed is:

1. A drop weight tower for initiating a crack in a material sample for fracture mechanics testing, the drop weight tower comprising:
   (a) a base having a top surface, and a sample holder mounted on the top surface for gripping the sample;
   (b) an attachment column extending upward from the top surface of the base at a first vertical location, the attachment column including a linear rail;
   (c) a carriage assembly attached to the linear rail of the attachment column, the carriage assembly including:
      (i) a carriage capable of sliding up and down along the linear rail of the attachment column; and
      (ii) a stage extending perpendicular to the linear rail, the stage having a first end that is attached to the carriage, a second end distal from the carriage, a top surface, and a bottom surface;
   (d) a razor blade holder on the bottom surface at the second end of the stage, located over the sample holder;
   (e) a razor blade which is separable from the razor blade holder; and
   (f) a hammer assembly on the top surface at the second end of the stage in-line with the razor blade holder, comprising:
      (i) a vertical rod; and
      (ii) an annular weight surrounding the vertical rod and operable to slide along the vertical rod.

2. The drop weight tower of claim 1, wherein the annular weight is formed from a pipe concentrically surrounding the vertical rod and having a first threaded end and a second threaded end, and a weighted cylinder attached to the pipe.

3. The drop weight tower of claim 1, wherein the annular weight is formed from a weighted disc concentrically surrounding the vertical rod and a ball bearing assembly concentrically surrounding the vertical rod, the weighted disc being connected to the ball bearing assembly.

4. The drop weight tower of claim 1, wherein the hammer assembly further includes an adjustable stopper attached to the vertical rod above the annular weight, the adjustable stopper acting as a starting drop point for the annular weight.

5. The drop weight tower of claim 1, wherein the annular weight further includes a handle for lifting the annular weight.

6. The drop weight tower of claim 1, wherein the razor blade holder of the hammer assembly is a spring loaded clamp.

7. The drop weight tower of claim 1, further comprising a safety lever extending from the attachment column, the safety lever having a locked position for holding the carriage assembly at a specified height and an unlocked position for allowing the carriage assembly to move up and down the linear rail.

8. The drop weight tower of claim 1, further comprising a positioning fixture secured in the sample holder and adapted to mount the material sample in alignment with the razor blade and the razor blade holder.

9. The drop weight tower of claim 1, further comprising a pneumatic cylinder mounted proximate to the attachment column, the pneumatic cylinder being connected to a handle on the carriage assembly.

10. The drop weight tower of claim 8, wherein the pneumatic cylinder includes a valve for adjusting the air flow through the cylinder.

11. The drop weight tower of claim 1, wherein the sample holder is mounted on top of a support pier on which the sample holder can rotate.

12. The drop weight tower of claim 1, wherein the razor blade has a sharpness of about 30° to about 35°, as measured by the angle of the tip of the razor blade.

13. A method for initiating a crack in a material sample for fracture mechanics testing, the method comprising:
   receiving a drop weight tower that comprises:
      (a) a base having a top surface, and a sample holder mounted on the top surface for gripping the sample;
      (b) an attachment column extending upward from the top surface of the base at a first vertical location, the attachment column including a linear rail;
      (c) a carriage assembly attached to the linear rail of the attachment column, the carriage assembly including:
         (i) a carriage capable of sliding up and down along the linear rail of the attachment column; and
         (ii) a stage extending perpendicular to the linear rail, the stage having a first end that is attached to the carriage, a second end distal from the carriage, a top surface, and a bottom surface;
      (d) a razor blade holder on the bottom surface at the second end of the stage, located over the sample holder;
      (e) a razor blade mounted in the razor blade holder; and
      (f) a hammer assembly on the top surface at the second end of the stage in-line with the razor blade holder, comprising:
         (i) a vertical rod; and
         (ii) an annular weight surrounding the vertical rod and operable to slide along the vertical rod;
   mounting the material sample in the sample holder;
   lowering the carriage along the linear rail until the razor blade rests on the material sample;
   raising the annular weight to a desired height along the vertical rod; and
   initiating a crack in the material sample by releasing the annular weight to travel down the vertical rod to create an impact force that causes the razor blade to initiate the crack in the material sample.

14. The method of claim 13, further comprising using an adjustable stopper to mark the height from which the annular weight can be released.

15. The method of claim 13, further comprising raising the carriage assembly along the linear rail until a safety lever locks the carriage in place at a specified height.

16. The method of claim 13, further comprising providing a pneumatic cylinder attached to the carriage assembly to control the speed which the carriage assembly can vertically travel along the linear rail.

17. The method of claim 13, wherein the material sample is a thermoset polymer or a thermoplastic polymer.

18. The method of claim 13, wherein fracture toughness test results obtained have a standard deviation of 0.10 MPa·m$^{0.5}$ or lower.

19. The method of claim 13, wherein crack length test results obtained have a standard deviation of 0.15 mm or less, or a standard deviation of 0.12 mm or less.

20. The method of claim 13, wherein the sample holder is a positioning fixture on a rotating vise and further comprising aligning the material sample with the razor blade.

21. The method of claim 13, wherein (i) upper and lower limits are set to achieve a crack length (a) over specimen width (W) ratio (a/W) between 0.45 and 0.55, according to ASTM D5045; or (ii) wherein out-of-spec results are less than 10%.

\* \* \* \* \*